US010954509B2

(12) United States Patent
Bustamante et al.

(10) Patent No.: US 10,954,509 B2
(45) Date of Patent: *Mar. 23, 2021

(54) PARTITIONING OF DNA SEQUENCING LIBRARIES INTO HOST AND MICROBIAL COMPONENTS

(71) Applicant: The Board of Trustees of the Leland Stanford Junior University, Stanford, CA (US)

(72) Inventors: Carlos D. Bustamante, Emerald Hills, CA (US); Meredith L. Carpenter, San Mateo, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 463 days.

This patent is subject to a terminal disclaimer.

(21) Appl. No.: 15/583,928

(22) Filed: May 1, 2017

(65) Prior Publication Data
US 2017/0233724 A1 Aug. 17, 2017

Related U.S. Application Data

(63) Continuation of application No. 14/619,011, filed on Feb. 10, 2015, now Pat. No. 9,670,485.
(Continued)

(51) Int. Cl.
C12Q 1/68 (2018.01)
C12N 15/10 (2006.01)

(52) U.S. Cl.
CPC ..... C12N 15/1065 (2013.01); C12N 15/1006 (2013.01); C12N 15/1013 (2013.01)

(58) Field of Classification Search
None
See application file for complete search history.

(56) References Cited

U.S. PATENT DOCUMENTS 4,945,236 A 7/1990 Mogami et al.
5,272,338 A 12/1993 Winograd et al.
(Continued)

FOREIGN PATENT DOCUMENTS

WO WO 2013/164319 11/2013
WO WO 2014/182574 11/2014
WO WO-2014182574 A1 * 11/2014 ......... C12N 15/1006

OTHER PUBLICATIONS

Kubota et al., "Improved In Situ Hybridization Efficiency with Locked-Nucleic-Acid-Incorporated DNA Probes," Applied and Environmental Microbiology, August, vol. 72, No. 8, pp. 5311-5317. (Year: 2006).*

(Continued)

Primary Examiner — Young J Kim
(74) Attorney, Agent, or Firm — James S. Keddie; Bozicevic, Field & Francis LLP

(57) ABSTRACT

Described herein is a method for isolating microbial DNA from a sample that comprises host DNA and microbial DNA. In some embodiments, the method may comprise: obtaining a tagged DNA sample, wherein the tagged DNA sample contains host DNA and microbial DNA, both comprising an appended universal adaptor; b) hybridizing the extracted DNA, in solution, with affinity-tagged RNA probes generated by in vitro transcribing, in the presence of an affinity-tagged ribonucleotide, a library of fragmented host DNA that has been ligated to an RNA promoter adaptor; c) binding the product of step b) with a capture agent that is tethered to a substrate, in the presence of RNA oligonucleotides that are complementary to or have the same sequence as one or more strands of the universal adaptor, thereby capturing the host DNA on the substrate; and d) collecting the unbound DNA, wherein the unbound DNA comprises the microbial DNA.

28 Claims, 3 Drawing Sheets

Specification includes a Sequence Listing.

Related U.S. Application Data

(60) Provisional application No. 61/940,375, filed on Feb. 15, 2014, provisional application No. 62/068,455, filed on Oct. 24, 2014.

(56) References Cited

U.S. PATENT DOCUMENTS

| | | | |
|---|---|---|---|
| 5,652,107 | A | 7/1997 | Lizardi et al. |
| 5,766,891 | A | 6/1998 | Shuman |
| 8,980,553 | B2 | 3/2015 | Feehery et al. |
| 9,670,485 | B2 * | 6/2017 | Bustamante ....... C12N 15/1065 |
| 2006/0110754 | A1 | 5/2006 | Nerenberg et al. |
| 2009/0195790 | A1 | 8/2009 | Zhu et al. |
| 2009/0209751 | A1 | 8/2009 | Brevnov et al. |
| 2010/0029498 | A1 | 2/2010 | Gnirke et al. |
| 2012/0178649 | A1 | 7/2012 | Watt et al. |
| 2012/0264122 | A1 | 10/2012 | Brentano et al. |
| 2012/0301043 | A1 | 11/2012 | Suga |
| 2013/0230857 | A1 | 9/2013 | Gnirke et al. |
| 2014/0031240 | A1 * | 1/2014 | Behlke ............... C12N 15/1003 506/2 |
| 2015/0360194 | A1 | 12/2015 | Bustamante et al. |

OTHER PUBLICATIONS

Wetmur, J.G., "DNA Probes: Applications of the Principles of Nucleic Acid Hybridization," Critical Reviews in Biochemistry and Molecular Biology, vol. 26, pp. 227-259. (Year: 1991).*

Nakamura et al., "How does RNase H recognize a DNA-RNA hybrid?", PNAS, USA, December, vol. 88, pp. 11535-11539. (Year: 1991).*

Carpenter, et al., "Pulling out the 1%: Whole-Genome Capture for the Targeted Enrichment of Ancient DNA Sequencing Libraries" The American Journal of Human Genetics 93: 852-864 (2013).

Gnirke, et al., "Solution Hybrid Selection with Ultra-long Oligonucleotides for Massively Parallel Targeted Sequencing" Nat Bitochenol. 27(2): 182-189, (2009).

Kidd, et al., "Exome capture from saliva produces high quality genomic and metagenomic data" BMC Genomics, 15:262 (2014).

Melnikov et al., "Hybrid selection for sequencing pathogen genomes from clinical samples", Genome Biology, 2011, 12:R73.

Feehery et al., "A method for Selectively Enriching Microbial DNA from Contaminating Vertebrate Host DNA", PLOS ONE, 2013, 8(10):e76096.

Lesnik et al., "Relative Thermodynamic Stability of DNA, RNA, and DNA:RNA Hybrid Duplexes: Relationship with Base Composition and Structure", Biochemistry, 1995, 34: 10807-10815.

* cited by examiner

Table 1

| PRE-CAP | Total Reads | Mapped to hg19 (#) | Mapped to hg19 (#) | Mapped to hg19 (% of total) | MAPQ>30 (% of total) | MAPQ>30 (% of total) | Percent decrease (%) |
|---|---|---|---|---|---|---|---|
| 1 (saliva) | 9,938,672 | 5,360,762 | 375,303 | 54% | 49% | 3% | 93.88% |
| 2 (cheek swab) | 7,675,354 | 3,416,389 | 1,977,480 | 45% | 40% | 22% | 45.00% |
| 3 (mock mix human/soil) | 9,259,376 | 2,716,454 | 1,534,674 | 29% | 27% | 18% | 33.33% |
| 4 (mock 2 mix human/soil) | 8,535,690 | 4,404,216 | 3,657,572 | 52% | 47% | 31% | 34.04% |

SEQUENCE LISTING

<160> NUMBER OF SEQ ID NOS: 7

<210> SEQ ID NO 1
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 1
gatcttaagg ctagagtact aatacgactc actataggt    40

<210> SEQ ID NO 2
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 2
ccctatagtg agtcgtatta gtactctagc cttaagatc    39

-continued

```
<210> SEQ ID NO 3
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 3
agtactaata cgactcacta tagg                                          24

<210> SEQ ID NO 4
<211> LENGTH: 86
<212> TYPE: DNA
<213> ORGANISM: Artificial Sequence
<220> FEATURE:
<223> OTHER INFORMATION: synthetic oligonucleotide

<400> SEQUENCE: 4
ctgtctctta tacacatctg acgctgccga cgagtgtaga tctcggtggt cgccgtatca   60
ttcctatagt gagtcgtatt agtact                                        86

<210> SEQ ID NO 5
<211> LENGTH: 88
<212> TYPE: DNA
<213> ORGANISM: artificial sequence
<220> FEATURE:
<223> OTHER INFORMATION: synthetic oligonucleotide
<220> FEATURE:
<221> NAME/KEY: misc_feature
<222> LOCATION: (35)..(40)
<223> OTHER INFORMATION: n is a, c, g, or t

<400> SEQUENCE: 5
ctgtctctta tacacatctc cgagcccacg agacnnnnnn atctcgtatg ccgtcttctg   60
cttgcctata gtgagtcgta ttagtact                                      88

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
aatgatacgg cgaccaccga                                               20

<210> SEQ ID NO 7
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 7
caagcagaag acggcatacg a                                             21
```

PARTITIONING OF DNA SEQUENCING LIBRARIES INTO HOST AND MICROBIAL COMPONENTS

CROSS-REFERENCING

This patent application is a continuation of U.S. patent application Ser. No. 14/619,011, filed on Feb. 10, 2015, which claims the benefit of US provisional patent application Ser. Nos. 61/940,375, filed on Feb. 15, 2014, and 62/068,455, filed on Oct. 24, 2014, all of which are incorporated by reference herein.

GOVERNMENT SUPPORT

This invention was made with Government support under grant nos. HG003229, HG005715 and HG007342 awarded by the National Institutes of Health (NIH). The Government has certain rights in the invention.

BACKGROUND

Low levels of microbial DNA in many human tissues has precluded the shotgun sequencing of many interesting samples for metagenomic analysis due to cost. For example, DNA libraries derived from whole human blood often contain >99% human DNA. Therefore, to detect an infectious agent circulating in human blood from shotgun sequencing, one would need to sequence to very high coverage in order to ensure sufficient coverage. Thus much of the cost associated with sequencing high human DNA samples provides relatively little metagenomic data. As a result many human tissue DNA samples are considered unsuitable for metagenomic sequencing merely because the data yield is low compared to the sequencing resources required. Thus there is a need in the art to increase microbial DNA yield in high host DNA samples and specifically to increase the percent of microbial DNA being sequenced when sequencing high host endogenous (HHE) DNA samples.

Recent developments in DNA extraction have provided lower cost next-generation sequencing techniques to the point that the field of metagenomics has transitioned from focusing on PCR-amplified 16S ribosomal RNA markers to shotgun sequencing of the whole metagenome. However shotgun sequencing can yield less than desirable results when sequencing HHE DNA samples due to the low percentage of microbial DNA in the overall sample material. Moreover, shotgun sequencing often fails to provide enough information to make an accurate resolution in metagenomic analysis especially when the selected molecules (e.g., 16S ribosomal RNA) represent only a single lineage. Furthermore, 16S ribosomal RNA lineages cannot often differentiate pathogenic from non-pathogenic strains of closely related bacteria, a key goal of clinical metagenomic analysis.

Instead the use of whole genome DNA and RNA sequences is preferred for metagenetic analysis because it provides information from the entire metagenome. Thus there is a need in the art to provide a DNA and RNA sequencing technique for metagenomic analysis in order to derive improved resolution. For example, whole genome analysis of metagenomes from the fecal material of obese and normal weight patients has revealed highly reproducible differences in microbial community structure. However, these materials tend to have very high microbial DNA content (>99% microbe and <1% human). In contrast, sequencing libraries derived from many other tissues including human blood, vagina, nasal mucosal membrane, and lung typically contain >90% human and <10% microbial DNA. While samples with <10% microbial DNA can still, with sufficient sequencing, yield enough information for metagenomic analyses, the required amount of sequencing of specimens with less target DNA is costly and thus untenable for many researchers.

SUMMARY

Described herein, among other thins, is a method for isolating microbial DNA from a sample that comprises host DNA and microbial DNA. In some embodiments, the method may comprise: obtaining a tagged DNA sample, wherein the tagged DNA sample contains host DNA and microbial DNA (where the DNA can be, e.g., genomic DNA or cDNA copied from RNA), both comprising an appended universal adaptor; b) hybridizing the extracted DNA, in solution, with affinity-tagged RNA probes generated by in vitro transcribing, in the presence of an affinity-tagged ribonucleotide, a library of fragmented host DNA that has been ligated to an RNA promoter adaptor; c) binding the product of step b) with a capture agent that is tethered to a substrate, in the presence of RNA oligonucleotides that are complementary to or have the same sequence as one or more strands of the universal adaptor, thereby capturing the host DNA on the substrate; and d) collecting the unbound DNA, wherein the unbound DNA comprises the microbial DNA.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
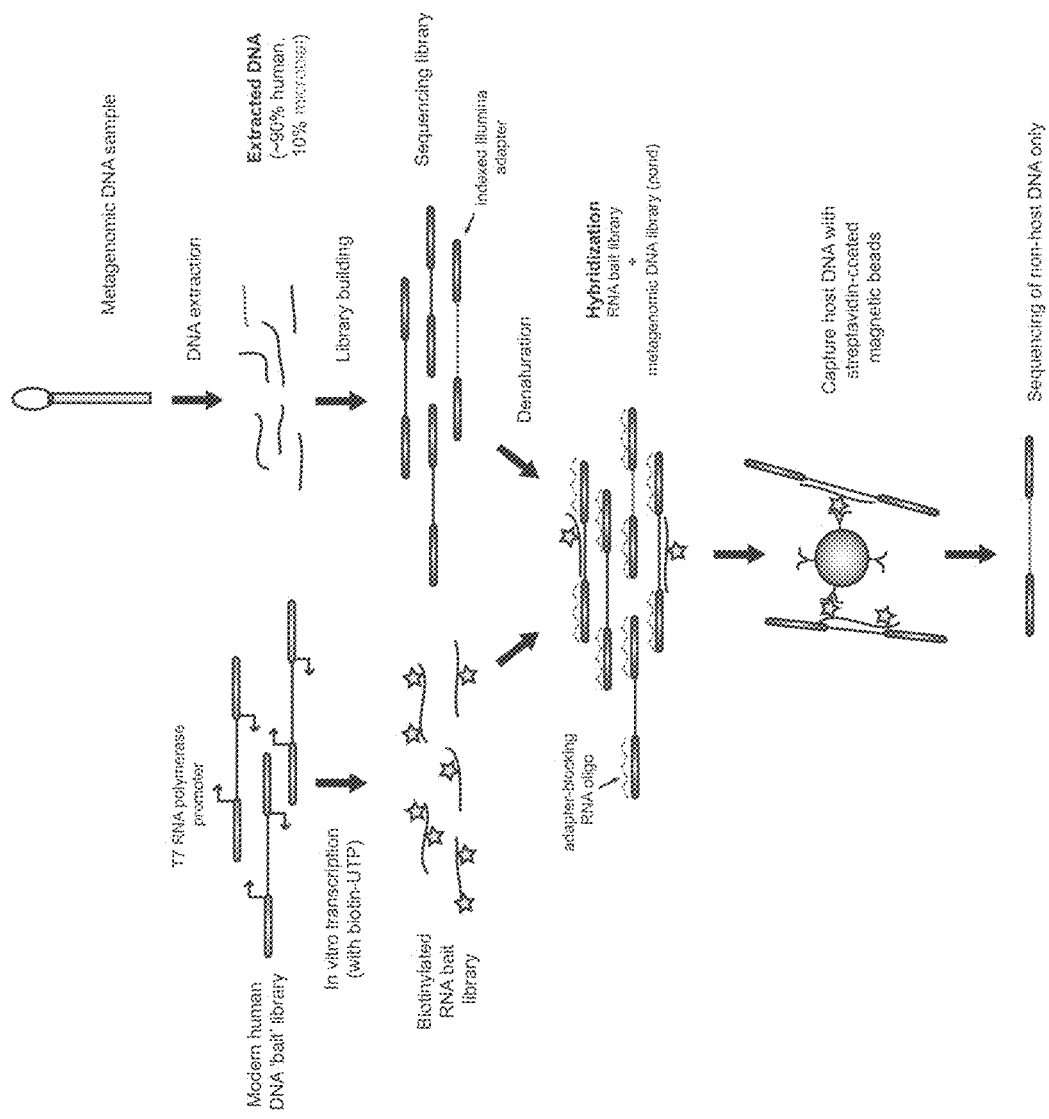
FIG. 1 is a schematic representation of a whole-genome host depletion process according to one implementation of the present method.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "sample" as used herein relates to a material or mixture of materials, typically, although not necessarily, in liquid form, containing one or more analytes of interest. In many cases, a sample may be obtained from a multicellular eukaryote (e.g., a human), and the sample contains DNA from the eukaryote as well as microbial DNA.

The term "nucleic acid sample," as used herein denotes a sample containing nucleic acids. Nucleic acid samples used herein may be complex in that they contain multiple different molecules that contain sequences. Genomic DNA from a mammal (e.g., mouse or human) are types of complex samples. Complex samples may have more then $10^4$, $10^5$, $10^6$ or $10^7$ different nucleic acid molecules.

The term "DNA" in the context of a DNA sample, is intended to encompass DNA isolated from a sample as well as cDNA that is copied from RNA isolated from a sample.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA. Also included in this definition are ZNAs, i.e., zip nucleic acids.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) and/or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The term "hybridization" refers to the process by which a strand of nucleic acid joins with a complementary strand through base pairing as known in the art. A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to generating one or more copies of a target nucleic acid, using the target nucleic acid as a template.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6$ $(\log_{10}[Na^+])+0.41$ (fraction G+C)−(60/N), where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N. Y., Ch. 10). Other formulas for predicting $T_m$ of oligonucleotide duplexes exist and one formula may be more or less appropriate for a given condition or set of conditions.

The term "partitioning," with respect to a genome, refers to the separation of one part of the genome from the remainder of the genome to produce a product that is isolated from the remainder of the genome. The term "partitioning" encompasses enriching.

The term "genomic region," as used herein, refers to a region of a genome, e.g., an animal or plant genome such as the genome of a human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example.

The term "genomic sequence," as used herein, refers to a sequence that occurs in a genome. Because RNAs are transcribed from a genome, this term encompasses sequence that exist in the nuclear genome of an organism, as well as sequences that are present in a cDNA copy of an RNA (e.g., an mRNA) transcribed from such a genome.

The term "genomic fragment," as used herein, refers to a region of a genome, e.g., a microbial, an animal or a plant genome such as the genome of a human, monkey, rat, fish or insect or plant. A genomic fragment may be an entire chromosome, or a fragment of a chromosome. A genomic fragment may be adaptor ligated (in which case it has an adaptor ligated to one or both ends of the fragment, or to at least the 5' end of a molecule), or may not be adaptor ligated.

In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example. Such an oligonucleotide may be employed in an assay that uses a sample containing a test genome, where the test genome contains a binding site for the oligonucleotide.

As used herein, the term "biotin moiety" refers to an affinity agent that includes biotin or a biotin analogue such as desthiobiotin, oxybiotin, 2-iminobiotin, diaminobiotin, biotin sulfoxide, biocytin, etc. Biotin moieties bind to streptavidin with an affinity of at least $10^{-8}$ M. A biotin affinity agent may also include a linker, e.g., -LC-biotin, -LC-LC-Biotin, -SLC-Biotin or -$PEG_n$-Biotin where n is 3-12.

The term "ligating," as used herein, refers to the enzymatically catalyzed joining of the terminal nucleotide at the 5' end of a first DNA molecule to the terminal nucleotide at the 3' end of a second DNA molecule. A transposase can catalyze a ligation.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary," each base of one of the nucleic acids base pairs with corresponding nucleotides in the other nucleic acid. Two nucleic acids do not need to be perfectly complementary in order to hybridize to one another.

The term "separating," as used herein, refers to physical separation of two elements (e.g., by size or affinity, etc.) as well as degradation of one element, leaving the other intact.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. Until they become covalently linked, the first and second strands are distinct molecules. For ease of description, the "top" and "bottom" strands of a double-stranded nucleic acid in which the top and bottom strands have been covalently linked will still be described as the "top" and "bottom" strands. In other words, for the purposes of this disclosure, the top and bottom strands of a double-stranded DNA do not need to be separated molecules. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand. If an oligonucleotide binds or anneals to both strands of a double-stranded DNA, the oligonucleotide may have two regions, a first region that hybridizes with the top strand of the double-stranded DNA, and a second region that hybridizes with the bottom strand of the double-stranded DNA.

The term "double-stranded DNA molecule" refers to both double-stranded DNA molecules in which the top and bottom strands are not covalently linked, as well as double-stranded DNA molecules in which the top and bottom stands are covalently linked. The top and bottom strands of a double-stranded DNA are base paired with one other by Watson-Crick interactions.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the $T_m$ of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired). Nucleic acid may also be denatured chemically (e.g., using urea or NaOH).

The term "genotyping," as used herein, refers to any type of analysis of a nucleic acid sequence, and includes sequencing, polymorphism (SNP) analysis, and analysis to identify rearrangements.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies.

The term "host DNA" refers to DNA that originates from the multicellular eukaryotic subject from which the sample was obtained. Host DNA can be, e.g., plant or animal, including mammals particularly humans. The term "host DNA" includes nuclear DNA as well as DNA present in other organelles, e.g., the mitochondria and chloroplast (if the host is a plant), but not the DNA from microbes that often grow on or in the subject. The term "host DNA" is intended to include cDNA copied from RNA that originates from the multicellular eukaryotic subject.

The term "microbial DNA" refers to genomic DNA that is microbial in origin (e.g., from a bacterium, virus or eukaryotic pathogen such as *Plasmodium, Leishmania*, or *Trypanosome*) that is present in a sample. In samples that contain both host and microbial DNA, the host and microbe may have, for example, a host-pathogen relationship or a symbiotic relationship. In some cases, the microbial fraction of a total DNA sample is obtained from a host may be derived from the microbiome that is associated with the host. The term "microbial DNA" is intended to include cDNA copied from RNA that originates from the multicellular eukaryotic subject.

The term "adaptor" refers to a nucleic acid that is ligatable to both strands of a double-stranded DNA molecule. In one embodiment, an adaptor may be a hairpin adaptor (i.e., one molecule that base pairs with itself to form a structure that has a double-stranded stem and a loop, where the 3' and 5' ends of the molecule ligate to the 5' and 3' ends of the double-stranded DNA molecule, respectively). In another embodiment, an adaptor may be a Y-adaptor. In another embodiment, an adaptor may itself be composed of two distinct oligonucleotide molecules that are base paired with one another. As would be apparent, a ligatable end of an adaptor may be designed to be compatible with overhangs made by cleavage by a restriction enzyme, or it may have blunt ends or a 5' T overhang. The term "adaptor" refers to double-stranded as well as single-stranded molecules. An adaptor can be DNA or RNA, or a mixture of the two. An adaptor containing RNA may be cleavable by RNase treatment or by alkaline hydrolysis. An adaptor may be 15 to 100 bases, e.g., 50 to 70 bases, although adaptors outside of this range are envisioned.

The term "adaptor-ligated," as used herein, refers to a nucleic acid that has been ligated to an adaptor. The adaptor can be ligated to a 5' end and/or a 3' end of a nucleic acid molecule.

The term "tagged DNA" as used herein refers to DNA molecules that have an added adaptor sequence, i.e., a "tag" of synthetic origin. An adaptor sequence can be added (i.e., "appended") by ligation. The term "universal adaptor" refers to an adaptor that is ligated to both ends of the nucleic acid molecules under study. In certain embodiments, the universal adaptor may be a Y-adaptor Amplification of nucleic acid molecules that have been ligated to Y-adaptors at both ends results in an asymmetrically tagged nucleic acid, i.e., a nucleic acid that has a 5' end containing one tag sequence and a 3' end that has another tag sequence.

The term "Y-adaptor" refers to an adaptor that contains: a double-stranded region and a single-stranded region in which the oligonucleotides are not complementary. The end of the double-stranded region ligates to target molecules such as double-stranded fragments of genomic DNA. Each strand of an adaptor-tagged double-stranded DNA that has been ligated to a Y adaptor is asymmetrically tagged in that it has the sequence of one strand of the Y-adaptor at one end and the other strand of the Y-adaptor at the other end.

The term "RNA promoter adaptor" is an adaptor that contains a promoter for a bacteriophage RNA polymerase, e.g., the RNA polymerase from bacteriophage T3, T7, SP6 or the like.

The term "capture tag" refer to a moiety that is capable of: a) specifically binding to binding partner for the capture tag non-covalently (i.e., is an "affinity tag") or b) selectively reacting with another chemoselective group to form a covalent bond (i.e., is a "chemoselective tag"). Examples of pairs of suitable affinity tags/binding parts are numerous and include, but are not limited to: biotin/streptavidin, biotin/avidin, digoxigenin/anti-digoxigenin antibody, and fluorescein/anti-fluorescein antibody, although many others are known. Examples of chemoselective reactive groups that selectively react with one another to form a covalent bond are numerous and include: amines and active esters such as an NHS esters, thiols and maleimide or iodoacetamide), as well as groups that can react with one another via Click chemistry, e.g., azide and alkyne groups.

The term "biotinylated ribonucleotide" refers to a ribonucleotide triphosphate (e.g., ATP, GTP, CTP and UTP) that is linked to a biotin moiety. Bio-16-UTP (Biotin-16-uridine-5'-triphosphate) is an example of a biotinylated ribonucleotide that can replace UTP for in vitro transcription reaction catalyzed by T3, T7 or SP6 RNA polymerases.

Other definitions of terms may appear throughout the specification.

DESCRIPTION OF EXEMPLARY EMBODIMENTS

An example of the method is shown in FIG. 1. In this example, the method starts by obtaining a DNA sample, wherein the DNA sample contains host DNA and microbial DNA. In certain cases, this may be done by extracting total DNA from a sample that comprises host DNA and microbial DNA to produce extracted DNA. In alternative embodiments, the DNA sample may be obtained by a) extracting RNA from said sample to produce extracted RNA; b) making cDNA from the extracted RNA; and c) ligating a universal adaptor to the cDNA.

In these embodiments, the extracted DNA may comprise more (at least 2 times, at least 5 times, at least 10 times, at least 50 times, or at least 100 times, at least 500 times or at least 1,000 times more) host DNA than microbial DNA. Methods for extracting total DNA and RNA from various samples, e.g., clinical, forensic, and environmental samples, are well known in the art. Samples include, but are not limited to, skin swab, skin biopsy, saliva, tooth swab, tooth scrapping, cheek swabs, throat swab, sputum, endogastric sample, feces, urine, vaginal, cervical, endocervical, endometrial, nasal swab, lung, organ biopsy, and tissue biopsy. A sample can also be a bodily fluid. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit and urine. In particular embodiments, the sample may be a clinical sample, e.g., a sample collected from a patient. In certain cases, the DNA in these samples may be highly fragmented, e.g., to an average size in the range of 10 bp to 5 kb, e.g., 20 bp to 200 bp and in certain cases may be fragmented after it is isolated. Methods for extracting total DNA from such samples are well known.

After obtaining the DNA sample, the DNA is ligated to a universal adaptor, i.e., an adaptor that ligates to both ends of the fragments of DNA contained in the extracted DNA sample. In certain cases, the universal adaptor may be a Y-adaptor, an example of which is described below. In particular cases, the ligating may be done by polishing the ends of the extracted DNA using a polymerase, and then ligating the adaptor via a blunt-end ligation. In other embodiments, the ends may be polished using Taq polymerase, which adds an additional 3' A (thereby producing a 3' A overhang), and the ligating may be done using an adaptor that has a 5' T overhang. As would be apparent, the adaptor may be "indexed" in that it contains a molecular barcode that identifies the sample to which it was ligated (which allows samples to be pooled before sequencing). Alternatively or in addition, the adaptor may contain a random barcode or the like. Such an adaptor can be ligated to the fragments and substantially every fragment corresponding to a particular region is tagged with a different sequence. This allows for identification of PCR duplicates and allows molecules to be counted.

After adaptor ligation, the sample may be optionally amplified, by PCR, for example. In these embodiments, the adaptor-ligated nucleic acids in the sample may be amplified using one or more primers that hybridize to the added adaptors (or their complements). In embodiments in which Y-adaptors are added, the adaptor-ligated nucleic acids may be amplified by PCR using two primers: a first primer that hybridizes to the single-stranded region of the top strand of the adaptor, and a second primer that hybridizes to the complement of the single-stranded region of the bottom strand of the adaptor. After the adaptors have been added to the nucleic acid in the sample and the adaptor-ligated nucleic acid has been optionally amplified, the adaptor-ligated nucleic acid may be hybridized in solution under high stringency with affinity-tagged RNA probes that have been generated by in vitro transcribing a library of host DNA that has been ligated to an RNA promoter adaptor (e.g., a T7 promoter), in the presence of an affinity-tagged ribonucleotide. The host DNA used in this step of the method should be made from a sample that is known to be free of microbial contamination. DNA isolated from cells grown in tissue culture could be used, for example. The host DNA used in this step may contain nuclear DNA and, optionally, DNA from other organelles, e.g., mictochondria The host DNA used in this step should be from the same species as the sample (e.g., if the sample is obtained from a human, then the host DNA used in this step should be human) In certain embodiments, the hybridization may be done by phenol emulsion reassociation (PERT) (Miller at al, Nucleic Acids Res. 1995 23: 2339-2340) or oscillating phenol emulsion reassociation (osPERT) (Bruzel et al Genomics. 2006 87:286-9) in order to reassociate the sequences rapidly.

In certain cases, the host DNA used in this step may be, for example, total eukaryotic (e.g., human) DNA that has been fragmented to a desired size, e.g., an average size in the range of 100 bp to 10 kb, e.g., 100 bp to 500 bp, although sizes outside of these ranges are envisioned. Such fragments may be made by fragmenting total DNA obtained from eukaryotic cells, e.g., cells grown in tissue culture, using physical methods (e.g., sonication, nebulization, or shearing), chemically, enzymatically (e.g., using a rare-cutting restriction enzyme) or using a transposable element. After fragmentation, the fragments may be ligated to an RNA polymerase promoter using conventional methods. The RNA polymerase promoter can also be added to the fragments during cleavage if a transposon is used. The fragments to which the RNA promoter has been ligated can then be transcribed in vitro into affinity-tagged RNA probes. In certain cases the host DNA used in this step of the method may be processed to select for or remove particular sequences prior to use.

After hybridization in solution, the host DNA in the sample is captured on a substrate, e.g., a solid support or beads. In these embodiments, the hybridized product is bound to a substrate that comprises a capture agent for the affinity tag, and the affinity tag binds to the capture agent. This step may be done in the presence of one or more RNA oligonucleotides that are complementary to or have the same sequence as one or more strands of the universal adaptor. In certain cases, these RNA oligonucleotides may themselves be made using in vitro transcription, e.g., by annealing two oligonucleotides together to produce a duplex that comprises a double-stranded RNA promoter upstream from a transcribed region, where the transcribed region can be transcribed to produce an RNA oligonucleotide. In these embodiments, the RNA oligonucleotides may be complementary to or have the same sequence as at least 50% (e.g., at least 60%, at least 70% or more) of the contiguous sequence of the universal adaptor. Next, the unbound DNA (i.e, the DNA that is not bound to the substrate) is collected. The unbound DNA comprises the microbial DNA.

After the microbial DNA has been isolated from the host DNA, it may be optionally amplified (e.g., using primers that hybridize to the added adaptor sequences or their complements) and sequenced. In certain embodiments, the isolated microbial DNA may be amplified using primers that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol Biol. 2009; 553:79-108); Appleby et al (Methods Mol Biol. 2009; 513: 19-39) and Morozova et al (Genomics. 2008 92:255-64), which are incorporated by reference for the general descriptions of the methods and the particular steps of the methods, including all starting products, reagents, and final products for each of the steps.

In another embodiment, the isolated microbial DNA may be sequenced using nanopore sequencing (e.g., as described in Soni et al. Clin Chem 2007 53: 1996-2001, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology is disclosed in U.S. Pat. Nos. 5,795,782, 6,015,714, 6,627,067, 7,238,485 and 7,258,838 and U.S. Pat Appln Nos. 2006003171 and 20090029477.

The isolated microbial fragments may be sequenced directly or, in some embodiments, the isolated microbial fragments may be amplified (e.g., by PCR) to produce amplification products that sequenced. In certain embodiments, amplification products may contain sequences that are compatible with use in, e.g., Illumina's reversible terminator method, Roche's pyrosequencing method (454), Life Technologies' sequencing by ligation (the SOLiD platform) or Life Technologies' Ion Torrent platform, as described above.

In certain embodiments, the sample sequenced may comprise a pool of nucleic acids from a plurality of samples, wherein the nucleic acids in the sample have a molecular barcode to indicate their source. In some embodiments the nucleic acids being analyzed may be derived from a single source (e.g., from different sites or a timecourse in a single subject), whereas in other embodiments, the nucleic acid sample may be a pool of nucleic acids extracted from a plurality of different sources (e.g., a pool of nucleic acids from different subjects), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed.

In certain cases, the captured (host) DNA can be released from the support, e.g., by denaturation, and also analyzed using similar methods. In these embodiments, the method may comprise releasing the host DNA from the substrate after the unbound DNA has been collected, i.e., after step d). In this embodiment, the method may comprise sequencing the host DNA released from the substrate.

The method described above may be used to isolate microbial DNA from a variety of different samples, which microbial DNA can be genotyped, e.g., sequenced, to investigate the individual from which the sample was obtained. In certain embodiments, the number of sequence reads and/or the number of random barcodes associated with a particular species of microbe may indicate the abundance of that species of microbe relative to other species of microbe in the sample.

In certain embodiments, the method may be employed to identify a microbial pathogen from a clinical sample. In these embodiments, the isolated nucleic acid may be sequenced, and the sequences may be compared to sequences from known pathogens, e.g., bacterial and viral pathogens, and, if a match is found, then the subject may be infected by that pathogen. In another embodiment, the method may be used for deep sequencing of a host-associated communities (a "microbiome"), with the advantage that the method enables sequencing of all microbial DNA in the sample, not only a subset of the DNA e.g., ribosomal DNA only.

Disease states may exhibit either the presence of a novel microbe(s), absence of a normal microbe(s), or an alteration in the proportion of microbes. Disease states may also have substantially similar microbial populations as normal states, but with a different microbial function or a different host response to the microbes due to environmental or host genetic factors.

For example, recent research has established that disruption of the normal equilibrium between a host and its microbiota, generally manifested as a microbial imbalance, is associated with, and may lead to, a number of conditions and diseases. These include Crohn's disease, ulcerative colitis, obesity, asthma, allergies, metabolic syndrome, diabetes, psoriasis, eczema, rosacea, atopic dermatitis, gastrointestinal reflux disease, cancers of the gastrointestinal tract, bacterial vaginosis, neurodevelopmental conditions such as autism spectrum disorders, and numerous infections, among others. For example, in Crohn's disease, concentrations of *Bacterioides*, Eubacteria and *Peptostreptococcus* are increased whereas *Bifidobacteria* numbers are reduced (Linskens et al., Scand J Gastroenterol Suppl. 2001; (234): 29-40); in ulcerative colitis, the number of facultative anaerobes is increased. In these inflammatory bowel diseases, such microbial imbalances cause increased immune stimulation, and enhanced mucosal permeability (Sartor, Proc Natl Acad Sci USA. 2008 Oct. 28; 105(43): 16413-4). In obese subjects, the relative proportion of Bacteroidetes has been shown to be decreased relative to lean people (Ley et al., Nature. 2006 Dec. 21; 444(7122): 1022-3), and possible links of microbial imbalances with the development of diabetes have also been discussed (Cani et al., Pathol Biol (Paris). 2008 July; 56(5): 305-9). In the skin, a role for the indigenous microbiota in health and disease has been suggested in both infectious and noninfectious diseases and disorders, such as atopic dermatitis, eczema, rosacea, psoriasis, and acne (Holland et al. Br. J. Dermatol. 96:623-626; Thomsen et al. Arch. Dermatol. 116:1031-1034; Till et al. Br. J. Dermatol. 142:885-892; Paulino et al. J. Clin. Microbiol. 44:2933-2941). Furthermore, the resident microbiota may also become pathogenic in response to an impaired skin barrier (Roth and James Annu Rev Microbiol. 1988; 42:441-64). Bacterial vaginosis is caused by an imbalance of the naturally occurring vaginal microbiota. While the normal vaginal microbiota is dominated by *Lactobacillus*, in grade 2 (intermediate) bacterial vaginosis, *Gardnerella* and *Mobiluncus* spp. are also present, in addition to *Lactobacilli*. In grade 3 (bacterial vaginosis), *Gardnerella* and *Mobiluncus* spp. predominate, and *Lactobacilli* are few or absent (Hay et al., Br. Med. J., 308, 295-298, 1994). Identification of which microbes are in a sample may aid in the diagnosis and treatment of such diseases.

In addition, the method may be used to detect an RNA virus or a reverse transcribing virus, e.g., reovirus, rotavirus, enterovirus, rhinovirus, hepatovirus, cardiovirus, aphthovirus, poliovirus, parechovirus, erbovirus, kobuvirus, teschovirus, coxsackie, norwalk virus, rubella virus, alphavirus, lymphocytic choriomeningitis virus, dengue virus, hepatitis C virus, yellow fever virus, influenzavirus A, influenzavirus B, influenzavirus C, isavirus, thogotovirus, measles virus, mumps virus, respiratory syncytial virus, Rinderpest virus, canine distemper virus, California encephalitis virus, hantavirus, rabies virus, Ebola virus, Marburg virus, corona virus, astrovirus, borna disease virus, arterivirus, equine arteritis virus, hepatitis E virus, retroviruses (e.g., HIV-1 and HIV-2) and hepatitis B virus. These and other uses of the method would be readily apparent.

In a first non-limiting illustrative embodiment of the present invention an in-solution whole-genome capture method is used to decrease the proportion of human DNA in metagenomic sequencing libraries in an unbiased manner According to the invention human genomic DNA libraries are created with adapters containing T7 RNA polymerase promoters in order to target as much of the host DNA in a given sample as possible. In a further step according to the invention an in vitro transcription of these libraries is performed with biotinylated dUTP in order to produce RNA probes or baits covering the entire human genome. The whole-genome capture method is particularly beneficial for substantially capturing only the human DNA in metagenomic human DNA samples.

Moreover, in an alternate method according to the present invention a less than whole-genome capture is usable to capture a particular set of genomes usable to analyze a particular aspect of the sample, e.g. specifically targeting a subset of microbial genomes such as only pathogenic genomes or other genome combinations. In particular those skilled in the art will recognize that genomic DNA libraries can be created with adapters containing T7 RNA polymerase promoters in order to target specific DNA portions without targeting the entire human metagenome.

In a further aspect of the invention the 'baits' are hybridized to human metagenomic libraries in solution and pulled down or captured with magnetic streptavidin-coated beads. All human DNA is bound, and the unbound metagenomic DNA is removed and amplified for sequencing. The capture process is shown schematically in FIG. 1 including the creation of the probe libraries. The in-solution capture protocol was adapted from a previously described protocol for exon capture.

EXAMPLES

Aspects of the present teachings can be further understood in light of the following examples, which should not be construed as limiting the scope of the present teachings in any way.

The capture method was tested on four metagenomic libraries: one saliva sample, one cheek swab, and two mock metagenomic samples created by combining human and soil DNA extract libraries.

The pre- and post-capture libraries were submitted for multiplexed sequencing on an Illumina MiSeq sequencer.

Figure 2:
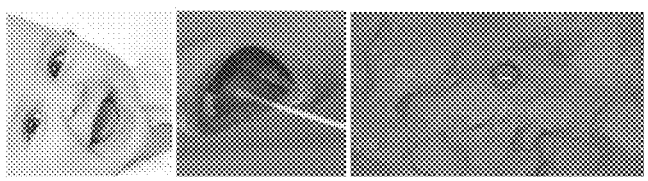
FIG. 2 depicts a table (Table 1) comparing sequencing results from 4 metagenomic DNA samples both before and after the whole-genome host depletion process according to the present invention.
Figure 3:
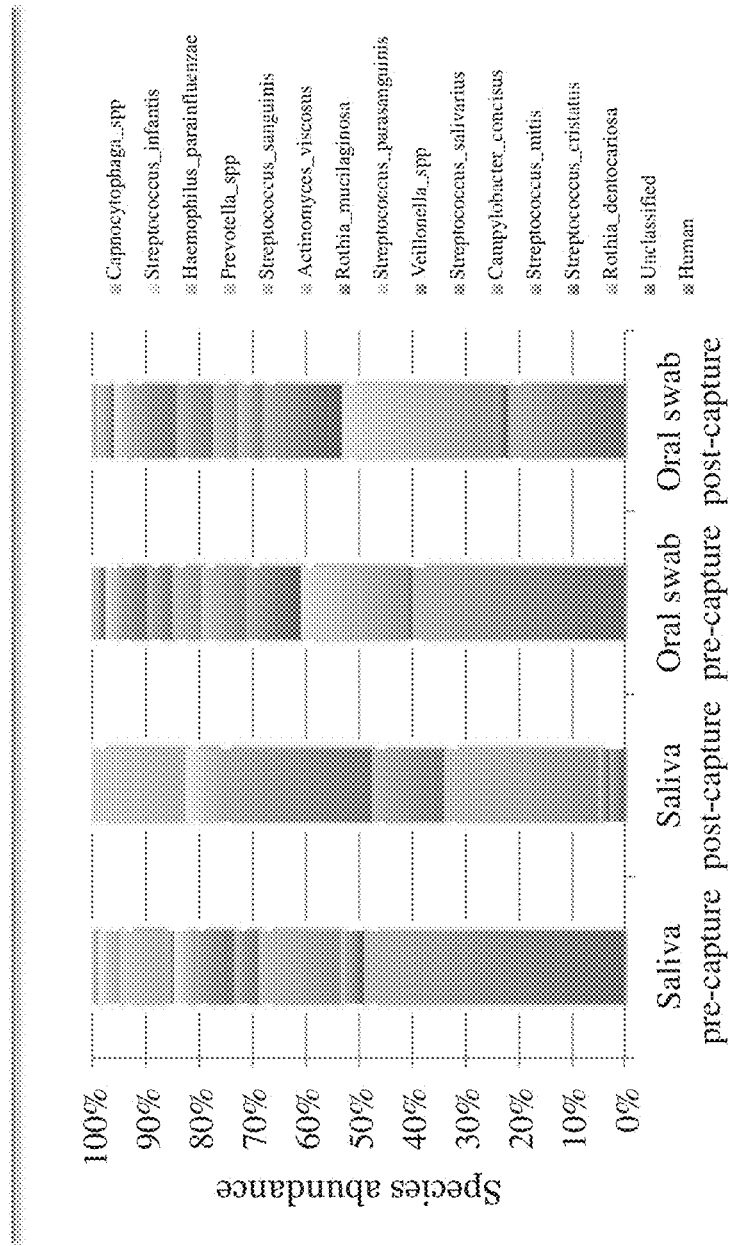
FIG. 3 depicts a stacked barchart of DNA composition by source (human and microbial) for the four samples in FIG. 2 analyzed by the present method.

The present method provides depletions ranging from 33-94% (see FIG. 2). For the saliva and swab samples, correlations between pre- and post-capture microbial contents ranged from 91-96%.

DNA Extraction and Library Preparation

DNA extractions from saliva and cheek swab samples were performed using a PowerSoil DNA Isolation Kit (MO-BIO) according to the manufacturer's instructions. Libraries were prepared using a Nextera library preparation kit (Epicentre) according to the manufacturer's instructions.

Preparation of RNA Probe Libraries

Five micrograms of human DNA (HapMap individual NA21732) was sheared on a Covaris S2 instrument with the following conditions: 8 min at 10% duty cycle, intensity 5, 200 cycles/burst, frequency sweeping. The resulting fragmented DNA (~150-200 bp average size, range 100-500) was subjected to end repair and dA-tailing using a KAPA library preparation kit (KAPA) according to the manufacturer's protocol. Ligation was also performed using this kit, but with custom adapters. T7 adapter oligos 1 and 2 (5'-GATCTTAAGGCTAGAGTACTAATACGACTCACTATA GGG*T-3' (SEQ ID NO: 1) and 5'-P-CCCTATAGT-GAGTCGTATTAGTACTCTAGCCTTAAGATC-3' (SEQ ID NO: 2)) were annealed by mixing a 12.5 µl of each 200 µM oligo stock with 5 µl of 10× buffer 2 (NEB) and 20 ul of $H_2O$. This mixture was heated to 95° C. for 5 minutes, then left on the bench to cool to room temperature for approximately 1 hour.

One microliter of this T7 adapter stock was used for the ligation reaction, again according to the library preparation kit instructions (KAPA). The libraries were then size-selected on a 2% agarose gel to remove unligated adapters and select for fragments ~200-300 bp in length (inserts ~120-220 bp). After gel extraction using a QIAquick Gel Extraction kit (Qiagen), the libraries were PCR-amplified in four separate reactions with the following components: 25 µl 2× HiFi HotStart ReadyMix (KAPA), 20 µl $H_2O$, 5 µl PCR primer (5'-GATCT-TAAGGCTAGAGTACTAATACGACTCACTATA GGG*T-3' (SEQ ID NO: 1), same as T7 oligo 1 above, 10 µM stock), and 5 µl purified ligation mix. The cycling conditions were as follows: 98° C./1 min, 98° C./15 s; 10 cycles of 60° C./15 s, 72° C./30 s; 72° C./5 min. The reactions were pooled and purified with AMPure XP beads (Beckman Coulter), eluting in 25 µl $H_2O$.

In Vitro Transcription

To transcribe the libraries into biotinylated RNA, we assembled the following in vitro transcription reaction mixture: 5 µl amplified library (~500 ng), 15.2 µl $H_2O$, 10 µl, 5× NASBA buffer (185 mM Tris-HCl, pH 8.5, 93 mM $MgCl_2$, 185 mM KCl, 46% DMSO), 2.5 µl0.1 M DTT, 0.5 µl 10 mg/ml BSA, 12.5 µl 10 mM dNTP mix (10 mM dATP, 10 mM dCTP, 10 mM dGTP, 6.5 mM dUTP, 2.5 mM biotin-16-UTP), 1.5 µl T7 RNA Polymerase (20 U/µl, Roche), 0.3 µl Pyrophosphatase (0.1 U/µl, NEB), and 2.5 µl SUPERase-In RNase inhibitor (20 U/µl, Life Technologies). The reaction was incubated at 37° C. overnight, treated for 15 min at 37° C. with 1 µl TURBO DNase (2 U/µl Life Technologies), then purified with an RNeasy Mini kit (Qiagen) according to the manufacturer's instructions, eluting twice in the same 30 µl of $H_2O$. A single reaction produced ~50 µg of RNA. The size of the RNA was checked by running ~100 ng on a 5% TBE/Urea gel and staining with ethidium bromide. For long-term storage, 1.5 µl of SUPERase-In was added, and the RNA was stored at −80° C.

Preparation of RNA Adapter Blockers

All of the captured aDNA libraries contained indexed Nextera adapters. To block these sequences and prevent nonspecific binding during capture, we created RNA adapter blockers, which can be produced in large amounts and are easy to remove by RNase treatment when capture is complete. The following oligonucleotides were annealed as described above: T7 universal promoter (5'-AGTACTAATACGACTCACTATAGG-3'; SEQ ID NO: 3)+either Nextera-block-P5 (5'-CTGTCTCTTATACA-CATCTGACGCT GCCGACGAGTGT AGATCTCGGTGGTCGCCGTATCATTCCTATAGT-GAGTCGTA TTAGTACT-3'; SEQ ID NO: 4) or Nextera-block-P7 (5'-CTGTCTCTTATACACATCTC CGAGCCCACGA GAC[NNNNNN] ATCTCGTATGCCGTCTTCTGCTTGCCTATAGTG AGTCGTATTAGTACT-3'; SEQ ID NO: 5), the latter containing random nucleotides at the site of the index sequence, which allows the same blockers to be used for all libraries.

For each of these double-stranded oligonucleotide solutions, 700 ng was subjected to in vitro transcription using a T7 High-Yield RNA Synthesis kit (NEB) according to the manufacturer's instructions. Following treatment with 1 µl of TURBO DNase (37° C./15 min), the RNA was purified with an RNeasy Mini kit according to the manufacturer's instructions, except that 675 µl of ethanol was added at step 2 of the protocol instead of 250 µl to ensure the retention of small RNAs. The RNA was eluted in 30 µl $H_2O$, to which 1.5 µl of SUPERase-In was added prior to storage at −80° C.

DNA Capture

Hybridization: The in-solution capture method was adapted from a protocol for exome capture[13]. For the pond, 12 µl of each aDNA library (~500 ng) was mixed in 200-µl PCR tubes. The RNA baits and blockers were mixed in a separate 1.5-ml tube as follows: for each capture, 5 µl (1000 ng) biotinylated RNA probe library, 1 µl SUPERase-In, 1 ul P5 block RNA (100 µM stock, see above), and 1 µl P7 block RNA (100 µM stock, see above). The DNA pond was heated in a thermal cycler to 95° C. for 5 min, followed by 65° C. for 5 min. When the DNA had been at 65° C. for 2.5 min, the RNA mix was heated to 65° C. for 2.5 min in a heat block. After the pond DNA had been at 65° C. for 5 min, 13 µl of prewarmed hybridization buffer (10×SSPE, 10×Denhardt's, 10 mM EDTA, 0.2% SDS, and 0.01% Tween 20) was added, followed by 7 µl RNA bait/block mix to produce 32-µl total reaction. The reaction was mixed by pipetting, then incubated at 65° C. for ~66 h.

Pulldown: For each capture reaction, 50 µl of Dynabeads MyOne Streptavidin C1 beads (Life Technologies) was mixed with 200 µl bead wash buffer (1 M NaCl, 10 mM Tris-HCl, pH 7.5, 1 mM EDTA, and 0.01% Tween 20), vortexed for 30 s, then separated on a magnetic plate for 2 minutes before removing the supernatant. This wash step was repeated twice, and after the last wash the beads were resuspended in 134 µl bead wash per sample. Next, 134 µl of bead solution was added to the 66 µl DNA/RNA hybridization mix, the solution was vortexed for 10 s, and the mix was incubated at room temperature for 30 minutes, vortexing occasionally. The mixture was then placed on a magnet to separate the beads, and the supernatant was removed and reserved. The beads were incubated in 165 µl low-stringency buffer (1×SSC/0.1% SDS/0.01% Tween 20) for 15 minutes at room temperature, followed by one 10-minute wash at 65° C. in 165 µl pre-warmed high-stringency buffer (0.1×SSC/0.1% SDS/0.01% Tween 20). The washes were also removed and reserved. Finally, the supernatant and two washes were concentrated using a MinElute PCR Purification Kit (Qiagen), eluting in 10 µl $H_2O$.

Amplification: The depleted libraries were PCR-amplified by combining the 10 µl of purified DNA (above) with 25 µl 2× KAPA HiFi Master Mix, 2 µl each primer (10 µM stocks of primer P5, 5'-AATGATACGGCGACCACCGA-3' (SEQ ID NO: 6), and P7, 5'-CAAGCAGAAGACGGCATACGA-3' (SEQ ID NO: 7)), 0.5 µl RNase A (7,000 U/ml, Qiagen), and 13 µl $H_2O$. Cycling conditions were as follows: 98° C./3 min; 9-15 cycles of 98° C./15 s, 60° C./20 s, 72° C./30 s; 72° C./2 min. The reactions were purified with MinElute columns.

Library Pooling and Multiplex Sequencing

The captured libraries were pooled in equimolar amounts and sequenced on a MiSeq sequencer (Illumina).

Mapping and Data Analysis

Reads were mapped to the human genome (hg19) using BWA version 0.5.9 using default settings. Duplicates were then removed using samtools (version 0.1.18), and reads were filtered for mapping qualities ≥30.

Metagenomic phylogenetic analysis was performed using MetaPhlAn.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations. Accordingly, the claims set forth below should be construed in view of the full breadth and spirit of the invention as disclosed herein.

What is claimed is:

1. A method for isolating microbial DNA from a sample that comprises host DNA and microbial DNA, comprising:
   a) obtaining a tagged DNA sample tagged with a universal adaptor, wherein the tagged DNA sample contains host DNA and microbial DNA which both comprise the universal adaptor;
   b) hybridizing the tagged DNA, in solution, with affinity-tagged oligonucleotide probes, wherein the affinity-tagged oligonucleotide probes comprise sequences complementary to sequences of the host DNA, and wherein the affinity-tagged oligonucleotide probes comprise affinity-tagged nucleotides;
   c) binding the product of step b) with a capture agent that is tethered to a substrate, in the presence of blocking oligonucleotides that are complementary to or have the same sequence as one or more strands of the universal adaptor, thereby capturing the host DNA on the substrate, wherein the blocking oligonucleotides are RNA oligonucleotides;
d) collecting the unbound DNA, wherein the unbound DNA comprises the microbial DNA;
e) treating the unbound DNA with an RNAse to degrade the RNA oligonucleotides; and
f) amplifying the collected DNA molecules after step e) by PCR (polymerase chain reaction) using a primer pair that comprises a primer that hybridizes to the universal adaptor.

2. The method of claim 1, wherein the sample is a clinical, forensic, or environmental sample.

3. The method of claim 1, wherein the sample is a swab of a surface of a human body.

4. The method of claim 1, wherein the sample is a bodily fluid.

5. The method of claim 1, wherein the tagged DNA sample comprises at least 2 times more host DNA than microbial DNA.

6. The method of claim 1, wherein the tagged DNA sample comprises at least 10 times more host DNA than microbial DNA.

7. The method of claim 1, further comprising sequencing the captured DNA molecules after step d).

8. The method of claim 1, wherein the hybridizing step b) is done by phenol emulsion reassociation (PERT) or oscillating phenol emulsion reassociation (osPERT).

9. The method of claim 1, wherein the method further comprises generating the affinity-tagged oligonucleotide probes of step b) by in vitro transcribing, in the presence of an affinity-tagged ribonucleotide, a library of fragmented host DNA that has been ligated to a promoter adaptor, and wherein the promoter is a T7 promoter.

10. The method of claim 1, wherein the substrate comprises magnetic beads.

11. The method of claim 1, wherein the universal adaptors are of 15 to 100 bases in length and are ligated to both ends of the DNA molecules in the tagged DNA.

12. The method of claim 1, wherein the affinity-tag is a biotin moiety and the capture agent is streptavidin or avidin.

13. The method of claim 1, wherein the blocking oligonucleotide is complementary to at least 50% of the sequence of the universal adaptor.

14. The method of claim 1, wherein the sample is obtained from a human.

15. The method of claim 1, wherein the microbial DNA comprises bacterial DNA.

16. The method of claim 1, wherein the tagged DNA sample comprises tagged genomic DNA.

17. The method of claim 1, wherein the step a) is done by:
a) extracting total DNA from the sample to produce extracted DNA; and
b) ligating a universal adaptor to the extracted DNA.

18. The method of claim 1, wherein the tagged DNA sample comprises tagged cDNA.

19. The method of claim 1, wherein the step a) is done by:
a) extracting RNA from the sample to produce extracted RNA;
b) making cDNA from the extracted RNA; and
c) ligating a universal adaptor to the cDNA.

20. The method of claim 1, further comprising releasing the host DNA from the substrate after step d).

21. The method of claim 20, further comprising sequencing the host DNA released from the substrate.

22. The method of claim 1, wherein the blocking oligonucleotides comprise naturally occurring nucleotides.

23. The method of claim 1, wherein the affinity tagged oligonucleotide probes comprise naturally occurring nucleotides.

24. The method of claim 23, wherein the naturally occurring nucleotides are selected from the group consisting of deoxyribonucleotides and ribonucleotides.

25. The method of claim 1, wherein the microbial DNA comprises viral DNA.

26. The method of claim 1, wherein the microbial DNA comprises DNA from a eukaryotic pathogen.

27. The method of claim 1, wherein sample comprises DNA isolated from blood plasma.

28. The method of claim 1, wherein sample comprises DNA isolated from saliva.

* * * * *